(12) United States Patent
Starnes

(10) Patent No.: US 7,655,017 B2
(45) Date of Patent: Feb. 2, 2010

(54) LANCET

(75) Inventor: Charles Starnes, Coral Srings, FL (US)

(73) Assignee: Carribean Medical Brokers, Inc., Coral Springs, FL (US)

( * ) Notice: Subject to any disclaimer, the term of this patent is extended or adjusted under 35 U.S.C. 154(b) by 416 days.

(21) Appl. No.: 10/735,094

(22) Filed: Dec. 11, 2003

(65) Prior Publication Data

US 2005/0131440 A1    Jun. 16, 2005

(51) Int. Cl.
*A61B 17/34* (2006.01)
(52) U.S. Cl. ........................................ 606/181
(58) Field of Classification Search ......... 606/181–185, 606/167; 76/119; 30/342, 343; 604/232, 604/240, 241
See application file for complete search history.

(56) References Cited

U.S. PATENT DOCUMENTS

| 5,385,571 | A |   | 1/1995 | Morita |
| 5,403,288 | A | * | 4/1995 | Stanners .................. 604/232 |
| 5,913,868 | A | * | 6/1999 | Marshall et al. ............. 606/181 |
| 6,723,111 | B2 | * | 4/2004 | Abulhaj et al. ............... 606/181 |

* cited by examiner

*Primary Examiner*—Kevin T Truong
(74) *Attorney, Agent, or Firm*—Thomas C. Saitta

(57) ABSTRACT

An improved lancet having a body integrally molded about an elongated shaft of a lancet needle and an easy twist off cap is disclosed. The lancet body further includes a cap integrally molded about the pointed end of the lancet needle and joined to the lancet body by a frangible junction connecting the distal end of the lancet body and the cap. The cap includes radially projecting, diametrically opposed tabs which provide structural members that may be grasped by the user to facilitate twisting and removal of the cap.

19 Claims, 3 Drawing Sheets

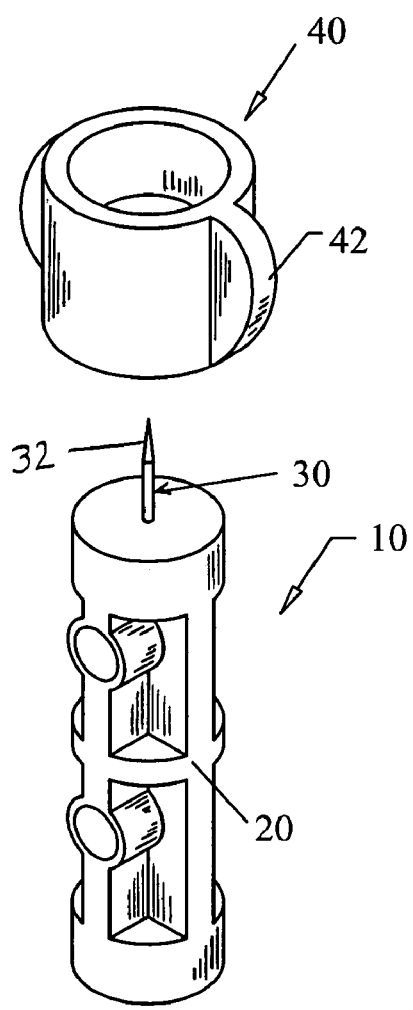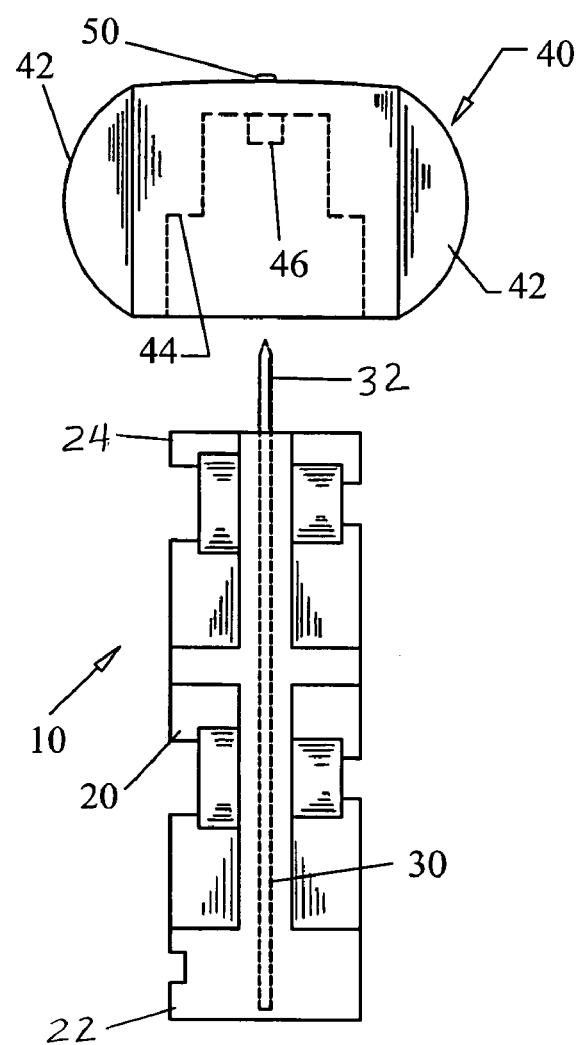
FIG. 4
FIG. 5

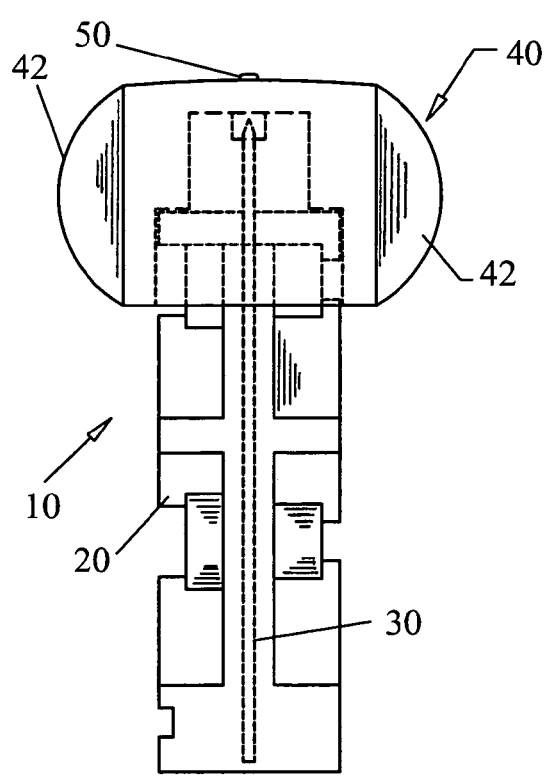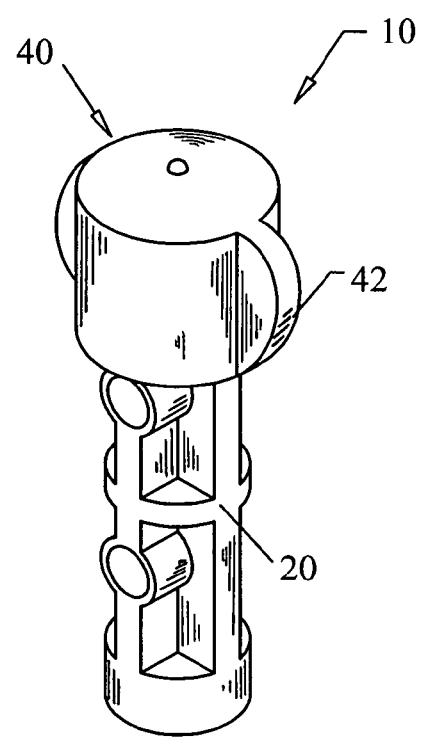
FIG. 6
FIG. 7

LANCET

CROSS REFERENCE TO RELATED APPLICATIONS

N/A

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights.

BACKGROUND OF THE INVENTION

1. Field of the Invention

The present invention relates to lancets of the type used to pierce the skin for obtaining a minute quantity of blood for analysis. More particularly, the present invention relates to a lancet assembly having an improved safety cap adapted for ease of removal and for secure closure and shielding of the contaminated lancet needle tip after use.

2. Description of the background art.

Lancets are often used to puncture the skin so as to facilitate the sampling of human blood for testing and/or analysis. For example, lancets are frequently used to obtain small amounts of blood by puncturing an appropriate area, such as the patient's fingertip. Blood samples obtained using lancets may be blotted or smeared onto various test strips or reagent pads in connection with various testing methods. For example, the blood of persons suffering from diabetes may be regularly tested using lancets to test glucose content. In addition, a wide variety of other tests may be employed using only small amounts of blood obtainable from lancet punctures.

Puncture wounds are commonly produced using disposable lancets. Such devices include a lancet body having a sharp pointed needle member that may be manipulated to produce a quick, and relatively painless, puncture of the patient's skin in order to produce at least a droplet of blood. An example of such a lancet is found in U.S. Pat. No. 3,358, 689, issued to Higgins, wherein a lancet needle is encased in an elongated plastic body with the needle tip embedded in a removable protective cap integrally molded with the plastic body to form a single integral unit prior to use.

Lancets are typically sterilized during production, and maintained in a sterile condition before use to prevent contamination of the lancet needle. In order to avoid contamination, lancets of the background art are manufactured with integral protective caps in order to prevent exposure and/or contamination of the lancet needle during post-manufacturing handling, shipping, and storage.

Lancets are commonly used in clinical and hospital settings by medical professionals, and are also used by individuals and patients outside of medical facilities, such as at home. Lancets may be used to puncture the patient's skin either alone by manual penetration, or in conjunction with a spring-loaded device developed to drive the lancet needle into the user's skin rapidly. Furthermore, due to concerns about communicable diseases transmitted through body fluids such as blood, the lancet must be carefully gripped to avoid contact with the sharp end of a lancet that has been contaminated with blood. Accordingly, after using the assembly, sufficient care must be taken by the user to avoid being punctured by a used lancet assembly, and the lancet assembly must be carefully handled until it is properly disposed.

As a result of these concerns, advances have been made in recent years to increase safety in handling such used devices. U.S. Pat. No. 5,385,571, issued to Moriata, discloses a lancet body having a needle end protruding from a lancet end, and a needle protector for protecting the needle. The needle protector comprises a cap or hood configured to tightly fit on the lancet end from which the needle end protrudes to insulate the needle end after use. The cap is integrally molded with the lancet body so as to be bonded to the top surface of the lancet body by a narrow neck. In order to use the lancet, the user must manually grasp and remove the cap, such as by twisting. Such is also the case with the lancet disclosed in U.S. Pat. No. 3,358,689, and most other lancets currently in use.

While the background art reveals a number of improvements directed to lancet designs, there exists a need for further improvements to facilitate ease of use. Specifically, it has been found that people often experience difficulty in removing the protective cap, due largely to the relatively small size of the lancet cap and the fact that lancet caps known in the art are not shaped to facilitate easy grasping and removal. Removal of the protective cap is particularly troublesome for the young, the elderly, and those suffering from injury or disease effecting use of the hands.

Accordingly, there exists a need for an improved lancet design that overcomes the disadvantages associated with the use of lancets of the background art.

BRIEF SUMMARY OF THE INVENTION

The present invention provides an improved lancet having a body integrally molded about an elongated shaft of a lancet needle. The lancet body includes a distal end from which the pointed needle end protrudes. The lancet body further includes a cap integrally molded about the pointed end of the lancet needle and joined to the lancet body by a narrow frangible junction connecting the distal end of the lancet body and the cap. The cap includes radially projecting, diametrically opposed tabs which provide structural members that may be grasped by the user to facilitate twisting and removal of the cap.

Accordingly, it is an object of the present invention to provide an improved lancet design.

Another object of the present invention is to provide an improved lancet design having integrally molded cap adapted for ease of removal.

Yet another object of the present invention is to provide a lancet having an integrally molded twist-off cap adapted with radially projecting tabs.

Still other features and advantages of the present invention will become apparent from consideration of the following specification and drawings.

BRIEF DESCRIPTION OF THE DRAWINGS

FIG. 4 is a perspective view thereof with the lancet cap exploded in a detached configuration;

FIG. 5 is a front view thereof;

FIG. 6 is a front view with the safety cap attached in covering relation with the lancet needle tip; and FIG. 7 is a perspective view thereof.

DETAILED DESCRIPTION OF THE PREFERRED EMBODIMENTS

Figure 1:
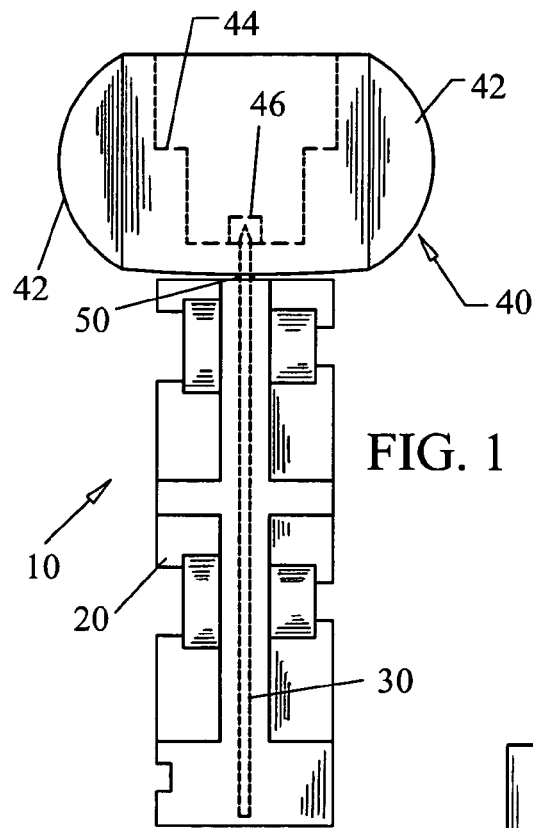
FIG. 1 is a front view of an improved lancet according to a preferred embodiment of the present invention as manufactured prior to usage.
Figure 2:
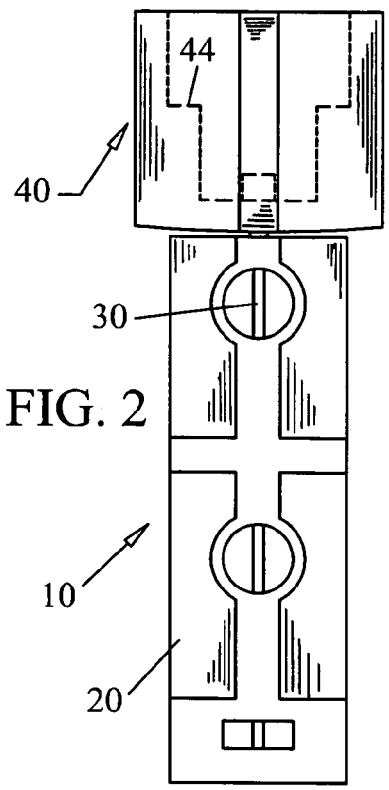
FIG. 2 is a right side view thereof.
Figure 3:
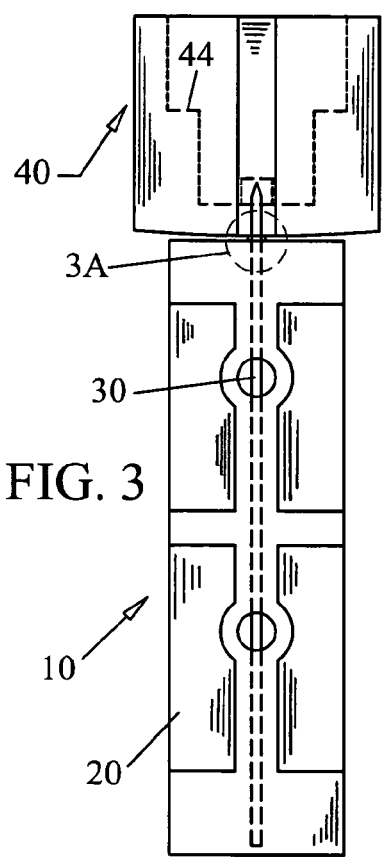
FIG. 3 is a left side view thereof.
Figure 3A:
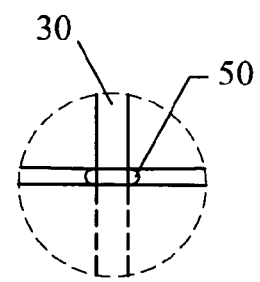
FIG. 3A depicts a partial detail view of the area identified as 3A in FIG. 3.

With reference now to the drawings, FIGS. 1-7 depict an improved disposable lancet, generally referenced as 10, according to a preferred embodiment of the present invention. Lancet 10 may be used manually by a user without additional apparatus to obtain a blood sample by piercing the user's fingertip, or may be used in conjunction with a mechanical apparatus. Lancet 10 includes an elongate molded body 20 having a proximal end 22 and a distal end 24. Body 20 includes an elongated rigid, slender tubular shaft 30 with a hypodermic needle-style piercing tip 32 projecting axially from distal 24 of body 20. Body 20 may be adapted to define any suitable structure to facilitate use thereof with a mechanical device. Lancet body 20 further includes a cap 40 integrally molded about piercing tip 32 during manufacturing. Cap 40 is further integrally molded and joined to lancet body 20 by a frangible junction 50 connecting distal end 24 of body with outer top surface of cap 40 as best depicted in FIGS. 1-3, with junction 50 shown in a detailed view in FIG. 3A.

FIGS. 1-3 depict the improved disposable lancet 10 in the "as manufactured" configuration. More particularly, body 20 and cap 40 are integrally molded in surrounding relation with sterilized needle shaft 30 and piercing tip 32 during the manufacturing process. As best depicted in FIG. 1, the portion of the needle that projects from the distal end 24 of body 20, namely piercing tip 32 is embedded within cap 40 and frangible junction 50. This configuration maintains needle 30 and particularly piercing tip 32 in a protective environment thereby preventing contamination during post manufacturing packaging, shipping, and storage. Cap 40 includes an inner axially projecting post 46 that receives the distal end of piercing tip 32 embedded therein in the pre-use, "as manufactured" configuration. Accordingly, the relative length of the projecting portion of piercing tip 32 is less than the combined length of frangible junction 50 and the top portion of cap 40 including projecting post 46.

A significant aspect of the present invention involves providing a lancet cap that is adapted for ease of removal. More particularly, cap 40 includes radially projecting, diametrically opposed tabs, referenced as 42, which function as structural members that may be grasped by the user and twisted to remove the cap. Tabs 42 preferably include arcuate peripheral edges as depicted in FIG. 1. Tabs 42 thus provide a user with projecting structures that may be grasped so as to enable twisting of cap 40 such that frangible junction 50 fails thereby releasing cap 40 from the detached configuration such that the cap may be separated from distal end 24 of body 20.

Cap 40 is also adapted to frictionally engage the distal end 24 of body 20 when cap 40 is reinstalled as shown in FIGS. 5-7 after lancet 10 is used so as to prevent blood from coming in contact with other persons and to help insure that no further contact is made with piercing tip 32. FIG. 5 depicts the cup-shaped cap positioned relative to body 20 prior to frictional engagement with the distal end 24 of body 20. Cap 40 is inverted relative to the pre-use configuration depicted in FIGS. 1-3, and aligned for engagement with body 20. Cap 40 includes an interior surface that defines an annular shoulder, referenced as 44. Cap shoulder 44 provides a stop surface that contacts the distal end 24 when body 20 is insertably engaged therewith. As previously discussed, cap 40 includes an inner axially projecting post 46 that receives the distal end of piercing tip 32 embedded therein in the pre-use, "as manufactured" configuration as depicted in FIGS. 1-3. Post 46 further functions to frictionally receive a portion of needle piercing tip 32 embedded therein when cap 40 is placed post-use onto the distal end 24 of body 20 as best illustrated in FIG. 6. Accordingly, cap 40 is securely maintained on body 20 by frictional engagement at multiple contact points, namely, between needle tip 32 and post 46, and between the inner circumferential side edge of cap 40 and the outer circumferential side edge of distal end 24 of body 20.

As should now be apparent, lancet 10 may be used by first disengaging cap 40 from body 20 wherein removal of the cap is accomplished by grasping cap tabs 42 and twisting so as to break frangible junction 50 thereby freezing cap 40 for separation and exposing piercing tip 32 of needle 30. Thereafter, lancet 10 may be used to puncture a person's skin either with or without the aid of a mechanical apparatus. After use, cap 40 is positioned as depicted in FIG. 5 and placed over distal end 24 of body 20 and pushed downward onto the lancet body such that the contaminated tip 32 pierces post 46 until cap shoulder 44 engages distal body end 24 thereby so as to stop further movement and terminate the capping procedure.

The instant invention has been shown and described herein in what is considered to be the most practical and preferred embodiment. It is recognized, however, that departures may be made therefrom within the scope of the invention and that obvious structural and/or functional modifications will occur to a person skilled in the art.

What I claim is:

1. A lancet having a pre-use and a post-use configuration, said lancet comprising:
   a lancet body having a distal end and a needle piercing tip projecting from said distal end;
   a cap, said cap in a pre-use configuration connected to said distal end by a frangible junction, said cap comprising an opening sized for mating engagement with said lancet distal end;
   an interior axially projecting post disposed within said opening of said cap, whereby said needle piercing tip is embedded within said interior axially projecting post in said pre-use configuration;
   said cap having at least one tab member projecting therefrom;
   wherein in a post-use configuration said frangible junction is broken and said cap is mounted onto said lancet body with said opening of said cap receiving said lancet distal end and at least a portion of said piercing tip embedded within said interior axially projecting post.

2. A lancet according to claim 1, wherein said cap is generally cylindrical and includes first and second diametrically opposed radially projecting tabs.

3. A lancet according to claim 1, wherein said cap defines an opening sized for mating engagement with said lancet distal end and an interior shoulder providing a stop upon engagement with said lancet distal end.

4. A lancet comprising:
   a lancet body having a distal end and a piercing tip projecting from said distal end;
   a cap connected to said distal end with said piercing tip embedded therein by a frangible junction, said cap comprising an opening facing in the distal direction away from said lancet body, said cap separable from said lancet body at said frangible junction such that said piercing tip is exposed;

whereby upon separation of said cap from said lancet body said cap is positionable upon said distal end of said lancet body such that said opening receives said distal end and said piercing tip is embedded in said cap.

5. The lancet of claim 4, wherein said cap is generally cylindrical and further comprises first and second diametrically opposed radially projecting tabs.

6. The lancet of claim 5, wherein said cap further comprises an interior shoulder providing a stop upon engagement with said lancet distal end.

7. The lancet of claim 4, wherein said cap further comprises an interior axially projecting post disposed within said opening for receiving at least a portion of said piercing tip embedded therein both when said cap is connected to said distal end and when said cap is positioned with said distal end received by said opening.

8. The lancet of claim 7, wherein said cap is generally cylindrical and further comprises first and second diametrically opposed radially projecting tabs.

9. The lancet of claim 8, wherein said cap further comprises an interior shoulder providing a stop upon engagement with said lancet distal end.

10. A lancet comprising:
an elongated lancet body having a distal end;
a shaft disposed within said lancet body, said shaft comprising a piercing tip projecting from said distal end of said lancet body; and
a removable cap having a first position connected to said distal end of said lancet body by a frangible junction with said piercing tip embedded within said frangible junction, said cap comprising a generally cylindrical opening coaxially aligned with said shaft and facing in the distal direction away from said lancet body
said cap being removable from said lancet body by destruction of said frangible junction, whereby said cap has a second position such that said opening of said cap is facing toward said lancet body such that said distal end of said lancet body is received by said opening and said piercing tip is embedded in said cap.

11. The lancet of claim 10, wherein said cap further comprises at least one tab member projecting therefrom.

12. The lancet of claim 10, wherein said cap further comprises first and second diametrically opposed radially projecting tabs.

13. The lancet of claim 12, wherein said cap further comprises an interior axially projecting post disposed within said opening for receiving at least a portion of said piercing tip embedded therein when said cap is in either said first or said second position.

14. The lancet of claim 10, wherein said cap further comprises an interior axially projecting post disposed within said opening for receiving at least a portion of said piercing tip embedded therein when said cap is in either said first or said second position.

15. A lancet comprising:
an elongated lancet body having a distal end;
a shaft disposed within said lancet body, said shaft comprising a piercing tip projecting from said distal end of said lancet body;
a removable cap connected to said distal end of said lancet body by a frangible junction with said piercing tip embedded therein, said cap comprising a generally cylindrical opening, said cap being generally cylindrical and coaxially aligned with said shaft prior to separation of said frangible junction and removal of said cap from said lancet body; and
at least one tab member projecting radially from said cap member.

16. The lancet of claim 15, said at least one tab member comprising first and second diametrically opposed radially projecting tabs.

17. The lancet of claim 16, said opening being coaxially aligned with said shaft prior to separation of said frangible junction and removal of said cap from said lancet body.

18. The lancet of claim 17, wherein said cap further comprises an interior axially projecting post disposed within said opening receiving at least a portion of said piercing tip embedded therein when said cap is removed from said lancet body, reversed and said opening is matingly engaged with said lancet distal end.

19. The lancet of claim 18, wherein said cap further comprises an interior shoulder providing a stop upon engagement with said lancet distal end.

* * * * *